(12) United States Patent
Nakayama

(10) Patent No.: US 9,341,567 B2
(45) Date of Patent: *May 17, 2016

(54) TERAHERTZ WAVE GENERATION DEVICE, LIGHT SOURCE DEVICE, CAMERA, IMAGING DEVICE, AND MEASUREMENT DEVICE

(75) Inventor: Hitoshi Nakayama, Chino (JP)

(73) Assignee: Seiko Epson Corporation (JP)

( * ) Notice: Subject to any disclaimer, the term of this patent is extended or adjusted under 35 U.S.C. 154(b) by 1031 days.

This patent is subject to a terminal disclaimer.

(21) Appl. No.: 13/405,434

(22) Filed: Feb. 27, 2012

(65) Prior Publication Data

US 2012/0236155 A1 Sep. 20, 2012

(30) Foreign Application Priority Data

Mar. 18, 2011 (JP) ................................ 2011-060429

(51) Int. Cl.
*G01J 5/10* (2006.01)
*G01N 21/3581* (2014.01)
(Continued)

(52) U.S. Cl.
CPC ............ *G01N 21/3581* (2013.01); *B82Y 20/00* (2013.01); *H01S 5/0057* (2013.01);
(Continued)

(58) Field of Classification Search
CPC ....................................... G01T 1/161
USPC ............... 250/338.1, 504 R, 338.4, 250, 393; 385/1, 2, 4, 8, 10, 12, 13, 40; 359/348, 359/339, 347, 337.5, 312
See application file for complete search history.

(56) References Cited

U.S. PATENT DOCUMENTS 3,983,406 A * 9/1976 Lax et al. ...................... 359/326
4,933,731 A * 6/1990 Kimura .......................... 257/438
(Continued)

FOREIGN PATENT DOCUMENTS

CN 101498879 A 8/2009
CN 101738380 A 6/2010
(Continued)

OTHER PUBLICATIONS

Extended European Search Report for Application No. EP 12 15 9857 dated Jan. 26, 2015 (9 pages).
(Continued)

*Primary Examiner* — David Porta
*Assistant Examiner* — Djura Malevic
(74) *Attorney, Agent, or Firm* — Harness, Dickey & Pierce, P.L.C.

(57) ABSTRACT

A terahertz wave generation device includes a light source device emitting an optical pulse, and an antenna generating a terahertz wave through irradiation of the optical pulse that is emitted from the light source device onto the antenna, wherein the light source device includes an optical pulse generation unit generating the optical pulse, a first pulse compression unit performing pulse compression based on saturable absorbers with respect to the optical pulse generated by the optical pulse generation unit, a second pulse compression unit performing pulse compression based on group velocity dispersion compensation with respect to the optical pulse already compressed by the first pulse compression unit, and an amplifying unit installed between the first pulse compression unit and the second pulse compression unit to amplify the optical pulse emitted from the first pulse compression unit.

30 Claims, 11 Drawing Sheets

(51) Int. Cl.
| | |
|---|---|
| *B82Y 20/00* | (2011.01) |
| *H01S 5/00* | (2006.01) |
| *H01S 5/06* | (2006.01) |
| *H01S 5/0625* | (2006.01) |
| *H01S 5/026* | (2006.01) |
| *H01S 5/065* | (2006.01) |
| *H01S 5/343* | (2006.01) |
| *H01S 5/40* | (2006.01) |

(52) U.S. Cl.
CPC ............. *H01S5/0265* (2013.01); *H01S 5/0609* (2013.01); *H01S 5/0625* (2013.01); *H01S 5/026* (2013.01); *H01S 5/0657* (2013.01); *H01S 5/34313* (2013.01); *H01S 5/4031* (2013.01)

(56) References Cited

U.S. PATENT DOCUMENTS

| | | | |
|---|---|---|---|
| 4,979,234 A * | 12/1990 | Agrawal et al. ............... 398/199 |
| 5,088,105 A | 2/1992 | Scifres et al. |
| 5,167,000 A * | 11/1992 | Minemoto et al. ............ 385/122 |
| 5,260,954 A * | 11/1993 | Dane et al. ....................... 372/25 |
| 5,274,495 A * | 12/1993 | Shirasaki ....................... 359/330 |
| 5,305,345 A * | 4/1994 | Albrecht et al. ................. 372/69 |
| 5,400,350 A | 3/1995 | Galvanauskas |
| 5,623,145 A | 4/1997 | Nuss |
| 5,640,480 A * | 6/1997 | Komine .......................... 385/122 |
| 5,689,361 A * | 11/1997 | Damen et al. .................. 359/284 |
| 5,710,430 A | 1/1998 | Nuss |
| 5,847,863 A * | 12/1998 | Galvanauskas et al. ... 359/341.3 |
| 5,880,887 A | 3/1999 | Goto |
| 6,014,249 A | 1/2000 | Fermann et al. |
| 6,078,416 A * | 6/2000 | Yano ............................... 398/154 |
| 6,081,361 A * | 6/2000 | Adams et al. .................. 398/201 |
| 6,243,517 B1 * | 6/2001 | Deacon ........................... 385/50 |
| 6,249,630 B1 | 6/2001 | Stock et al. |
| 6,324,204 B1 * | 11/2001 | Deacon ............................ 372/96 |
| 6,356,693 B1 * | 3/2002 | Shimizu et al. ................ 385/131 |
| 6,448,850 B1 * | 9/2002 | Yamada ........................... 330/44 |
| 6,587,488 B1 * | 7/2003 | Meissner et al. ........... 372/29.01 |
| 6,603,600 B2 * | 8/2003 | Pang ............................... 359/348 |
| 6,697,186 B2 * | 2/2004 | Kawase et al. ................ 359/330 |
| 6,934,313 B1 * | 8/2005 | Deacon ............................ 372/64 |
| 6,980,345 B2 * | 12/2005 | Kim et al. ...................... 359/248 |
| 7,088,756 B2 * | 8/2006 | Fermann et al. ......... 372/45.013 |
| 7,218,443 B2 * | 5/2007 | Tauser et al. .................. 359/337.5 |
| 7,386,018 B2 * | 6/2008 | Mori et al. ....................... 372/18 |
| 7,430,074 B2 * | 9/2008 | Korenblit et al. .............. 359/328 |
| 7,558,302 B1 * | 7/2009 | Delfyett et al. .................. 372/25 |
| 7,941,014 B1 * | 5/2011 | Watts et al. ..................... 385/32 |
| 8,053,732 B2 * | 11/2011 | Choi et al. .................. 250/341.1 |
| 8,093,560 B2 * | 1/2012 | Kuroyanagi et al. ...... 250/341.1 |
| 8,094,691 B2 * | 1/2012 | Harter et al. ..................... 372/25 |
| 8,150,271 B1 * | 4/2012 | Brennan et al. ............... 398/193 |
| 8,189,257 B2 * | 5/2012 | Rakich et al. ................. 359/337.5 |
| 8,189,971 B1 * | 5/2012 | Vaissie et al. ................... 385/37 |
| 8,208,196 B2 * | 6/2012 | Fermann et al. ............... 359/328 |
| 8,213,476 B1 * | 7/2012 | Wanke et al. ............. 372/45.012 |
| 8,274,058 B1 * | 9/2012 | Wanke et al. ................ 250/370.12 |
| 8,391,324 B2 * | 3/2013 | Kondo et al. .................... 372/18 |
| 8,405,031 B2 * | 3/2013 | Katagiri ....................... 250/338.4 |
| 8,774,240 B2 * | 7/2014 | Cheriaux ......................... 372/25 |
| 8,861,075 B2 * | 10/2014 | Dantus et al. ............... 359/337.5 |
| 8,878,134 B2 * | 11/2014 | Takenaka .................... 250/341.1 |
| 2001/0053008 A1 | 12/2001 | Ueno ............................. 359/158 |
| 2002/0171913 A1 * | 11/2002 | Batchko et al. ............... 359/333 |
| 2003/0012493 A1 * | 1/2003 | Lee et al. ......................... 385/28 |
| 2003/0156605 A1 * | 8/2003 | Richardson et al. ............. 372/25 |
| 2003/0189959 A1 * | 10/2003 | Erbert et al. ..................... 372/25 |
| 2003/0223673 A1 * | 12/2003 | Garito et al. ..................... 385/14 |
| 2004/0000942 A1 * | 1/2004 | Kapteyn et al. ............... 327/306 |
| 2004/0037497 A1 * | 2/2004 | Lee .................................. 385/28 |
| 2005/0121629 A1 * | 6/2005 | Unterrainer et al. ....... 250/504 R |
| 2005/0163426 A1 * | 7/2005 | Fermann et al. ................. 385/37 |
| 2005/0242287 A1 * | 11/2005 | Hakimi ..................... 250/363.09 |
| 2005/0271094 A1 * | 12/2005 | Miller et al. ..................... 372/25 |
| 2005/0281508 A1 * | 12/2005 | Krupkin et al. ................. 385/36 |
| 2006/0169677 A1 * | 8/2006 | Deshi .......................... 219/121.7 |
| 2006/0238854 A1 * | 10/2006 | Haidar et al. ................. 359/326 |
| 2006/0274403 A1 * | 12/2006 | Kaplan et al. ............... 359/337.1 |
| 2008/0023633 A1 * | 1/2008 | Mittleman et al. .......... 250/341.1 |
| 2008/0075134 A1 * | 3/2008 | Moeller ..................... 372/38.02 |
| 2008/0107377 A1 * | 5/2008 | Cho et al. ......................... 385/32 |
| 2008/0217538 A1 * | 9/2008 | Ouchi et al. ................. 250/338.4 |
| 2008/0232225 A1 * | 9/2008 | Cho et al. .................. 369/112.27 |
| 2008/0265165 A1 * | 10/2008 | Yeh et al. ..................... 250/341.1 |
| 2008/0315098 A1 * | 12/2008 | Itsuji ............................. 250/330 |
| 2009/0009190 A1 * | 1/2009 | Itsuji ............................. 324/639 |
| 2009/0015491 A1 | 1/2009 | Ikeda et al. |
| 2009/0141341 A1 * | 6/2009 | Gaudiosi et al. .............. 359/339 |
| 2009/0146084 A1 * | 6/2009 | Itsuji .......................... 250/503.1 |
| 2009/0213880 A1 | 8/2009 | Ouchi et al. |
| 2009/0232462 A1 * | 9/2009 | Creeden et al. ............... 385/122 |
| 2009/0251769 A1 * | 10/2009 | Kong et al. .................. 359/337.5 |
| 2009/0279167 A1 * | 11/2009 | Vigroux et al. ................ 359/347 |
| 2009/0296744 A1 * | 12/2009 | Dantus et al. .................... 372/5 |
| 2010/0053733 A1 * | 3/2010 | Falcoz et al. ................ 359/337.5 |
| 2010/0084570 A1 * | 4/2010 | Katagiri ..................... 250/458.1 |
| 2010/0244993 A1 * | 9/2010 | Sekiguchi et al. .......... 333/219.1 |
| 2010/0309545 A1 * | 12/2010 | Zaouter et al. ............. 359/337.5 |
| 2011/0026105 A1 * | 2/2011 | Bayramian et al. ........ 359/337.5 |
| 2011/0210252 A1 | 9/2011 | Ouchi et al. |
| 2012/0097850 A1 * | 4/2012 | Darcie et al. .................. 250/340 |
| 2012/0326036 A1 * | 12/2012 | Tomioka .................... 250/338.1 |
| 2013/0120584 A1 * | 5/2013 | Nakayama ..................... 348/164 |
| 2013/0153765 A1 * | 6/2013 | Tomioka ........................ 250/330 |
| 2013/0190628 A1 * | 7/2013 | Tripodi et al. ................. 600/476 |

FOREIGN PATENT DOCUMENTS

| | | |
|---|---|---|
| EP | 1087478 A1 | 3/2001 |
| EP | 2086074 A2 | 8/2009 |
| JP | 02-221902 | 9/1990 |
| JP | 04-036268 | 3/1992 |
| JP | 04-199133 | 7/1992 |
| JP | 08-320254 | 12/1996 |
| JP | 11-218628 | 8/1999 |
| JP | 3014039 | 12/1999 |
| JP | 2000-012977 A | 1/2000 |
| JP | 3328881 | 7/2002 |
| JP | 2006-024803 A | 1/2006 |
| JP | 3811564 | 6/2006 |
| JP | 2008-145289 A | 6/2008 |

OTHER PUBLICATIONS

C. Jordens et al., "All-Semiconductor Laser Driven Terahertz Time-Domain Spectrometer", Applied Physics B, Lasers and Optics, Springer, Berlin, Germany, vol. 93, No. 2-3, Sep. 17, 2008, pp. 515-520.

A. Penzkofer, "Passive Q-Switching and Mode-Locking for the Generation of Nanosecond to Femtosecond Pulses", Applied Physics B, Photophysics and Laser Chemistry, Springer, Berlin, Germany, vol. 46, No. 1, May 1, 1988, pp. 43-60.

* cited by examiner

TERAHERTZ WAVE GENERATION DEVICE, LIGHT SOURCE DEVICE, CAMERA, IMAGING DEVICE, AND MEASUREMENT DEVICE

The entire disclosure of Japanese Patent Application No. 2011-060429 filed Mar. 18, 2011 is incorporated herein by reference.

BACKGROUND

1. Technical Field

The present invention relates to a terahertz wave generation device, a light source device, a camera, an imaging device, and a measurement device.

2. Related Art

Terahertz waves have recently gained attention. Terahertz waves are electromagnetic waves having frequencies of equal to or greater than 100 GHz and equal to or less than 30 THz. The terahertz waves, for example, may be used for imaging, respective measurements such as spectroscopic measurements, nondestructive inspection, and the like.

A terahertz wave generation device that generates such a terahertz wave includes a light source device that generates an optical pulse having a pulse width on the order of subpico-seconds (several hundreds of femtoseconds), and an antenna that generates a terahertz wave through irradiation of the optical pulse that is generated from the light source device onto the antenna. As a light source device that generates an optical pulse having a pulse width on the order of subpico-seconds, a femtosecond fiber laser or a titanium sapphire laser is used.

However, if the femtosecond fiber laser or the titanium sapphire laser is used, the device becomes large. In order to miniaturize the device, a method of generating an optical pulse having a target pulse width using an optical pulse generation device that generates an optical pulse having a pulse width that is larger than the target pulse width and a pulse compression device that performs pulse compression with respect to the optical pulse generated by the optical pulse generation device has been adopted.

Such a pulse compression method may use saturable absorbers (for example, see Japanese Patent No. 3328881).

However, according to the method that uses the saturable absorbers, to obtain an optical pulse having a desired pulse width, it is necessary to make the optical pulse pass through plural saturable absorbers, and this causes the length of the light source device to become too long.

Another pulse compression method uses a group velocity dispersion compensation medium (for example, see Japanese Patent No. 3014039).

However, only an optical pulse having a desired pulse width may not be obtained by the method that uses the group velocity dispersion compensation medium.

SUMMARY

An advantage of some aspects of the invention is to provide a terahertz wave generation device, a light source device, a camera, an imaging device, and a measurement device, which can make a light source device smaller and thus can miniaturize the entire device.

An aspect of the invention is directed to a terahertz wave generation device, which includes a light source device emitting an optical pulse; and an antenna generating a terahertz wave through irradiation of the optical pulse that is emitted from the light source device onto the antenna, wherein the light source device includes an optical pulse generation unit generating the optical pulse; a first pulse compression unit performing pulse compression based on saturable absorbers with respect to the optical pulse generated by the optical pulse generation unit; a second pulse compression unit performing pulse compression based on group velocity dispersion compensation with respect to the optical pulse already compressed by the first pulse compression unit; and an amplifying unit installed at a front end of the first pulse compression unit or between the first pulse compression unit and the second pulse compression unit to amplify the optical pulse.

According to this aspect, since the light source device includes the first pulse compression unit and the second pulse compression unit, miniaturization of the device can be realized, the optical pulse having a desired pulse width at a desired height can be generated, and thus a desired terahertz wave can be certainly generated.

In the terahertz wave generation device according to the aspect of the invention, it is preferable that the first pulse compression unit or the amplifying unit have a waveguide which is bent at least once.

Accordingly, further miniaturization can be realized.

In the terahertz wave generation device according to the aspect of the invention, it is preferable that the light source device have a reflection film formed on the bent portion of the waveguide to reflect the optical pulse.

Accordingly, the optical pulse can be certainly reflected along the waveguide.

In the terahertz wave generation device according to the aspect of the invention, it is preferable that the light source device be provided with plural units each including the optical pulse generation unit, the first pulse compression unit, the second pulse generation unit, and the amplifying unit.

Accordingly, a high-output terahertz wave can be generated through irradiation of the optical pulse emitted from the respective units between a pair of common electrodes of the antenna.

Another aspect of the invention is directed to a camera, which includes a terahertz wave generation device emitting a terahertz wave; and a terahertz wave detection device detecting the terahertz wave that is emitted from the terahertz wave generation device and penetrates or is reflected from an object, wherein the terahertz wave generation device includes a light source device emitting an optical pulse; and an antenna generating a terahertz wave through irradiation of the optical pulse that is emitted from the light source device onto the antenna, wherein the light source device has an optical pulse generation unit generating the optical pulse; a first pulse compression unit performing pulse compression based on saturable absorbers with respect to the optical pulse generated by the optical pulse generation unit; a second pulse compression unit performing pulse compression based on group velocity dispersion compensation with respect to the optical pulse already compressed by the first pulse compression unit; and an amplifying unit installed at a front end of the first pulse compression unit or between the first pulse compression unit and the second pulse compression unit to amplify the optical pulse.

Accordingly, the camera having the above-described effect according to the aspect of the invention can be provided.

Still another aspect of the invention is directed to an imaging device, which includes a terahertz wave generation device emitting a terahertz wave; a terahertz wave detection device detecting the terahertz wave that is emitted from the terahertz wave generation device and penetrates or is reflected from an object; and an image generation unit generating an image of the object based on the result of the detection performed by the terahertz wave detection device, wherein the terahertz wave generation device includes a light source device emitting an optical pulse; and an antenna generating a terahertz wave through irradiation of the optical pulse that is emitted from the light source device onto the antenna, wherein the light source device has an optical pulse generation unit generating the optical pulse; a first pulse compression unit performing pulse compression based on saturable absorbers with respect to the optical pulse generated by the optical pulse generation unit; a second pulse compression unit performing pulse compression based on group velocity dispersion compensation with respect to the optical pulse already compressed by the first pulse compression unit; and an amplifying unit installed at a front end of the first pulse compression unit or between the first pulse compression unit and the second pulse compression unit to amplify the optical pulse.

Accordingly, the imaging device having the above-described effect according to the aspect of the invention can be provided.

Yet another aspect of the invention is directed to a measurement device, which includes a terahertz wave generation device emitting a terahertz wave; a terahertz wave detection device detecting the terahertz wave that is emitted from the terahertz wave generation device and penetrates or is reflected from an object; and a measurement unit measuring the object based on the result of the detection performed by the terahertz wave detection device, wherein the terahertz wave generation device includes a light source device emitting an optical pulse; and an antenna generating a terahertz wave through irradiation of the optical pulse that is emitted from the light source device onto the antenna, wherein the light source device has an optical pulse generation unit generating the optical pulse; a first pulse compression unit performing pulse compression based on saturable absorbers with respect to the optical pulse generated by the optical pulse generation unit; a second pulse compression unit performing pulse compression based on group velocity dispersion compensation with respect to the optical pulse already compressed by the first pulse compression unit; and an amplifying unit installed at a front end of the first pulse compression unit or between the first pulse compression unit and the second pulse compression unit to amplify the optical pulse.

Accordingly, the measurement device having the above-described effect according to the aspect of the invention can be provided.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, a terahertz wave generation device, a camera, an imaging device, and a measurement device according to preferred embodiments of the invention will be described in detail with reference to the accompanying drawings.

First Embodiment

Figure 1:
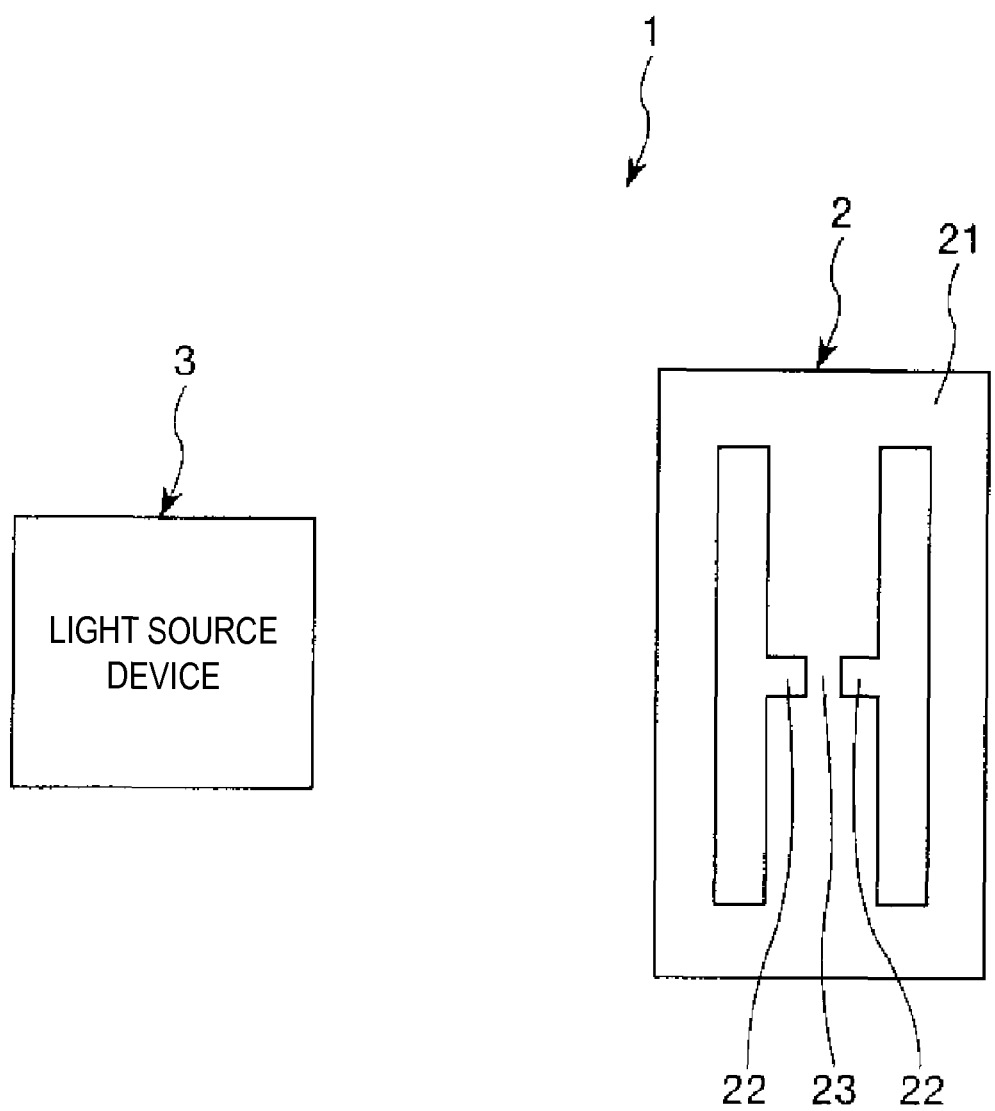
FIG. 1 is a diagram schematically showing a terahertz wave generation device according to a first embodiment of the invention.
Figure 2:
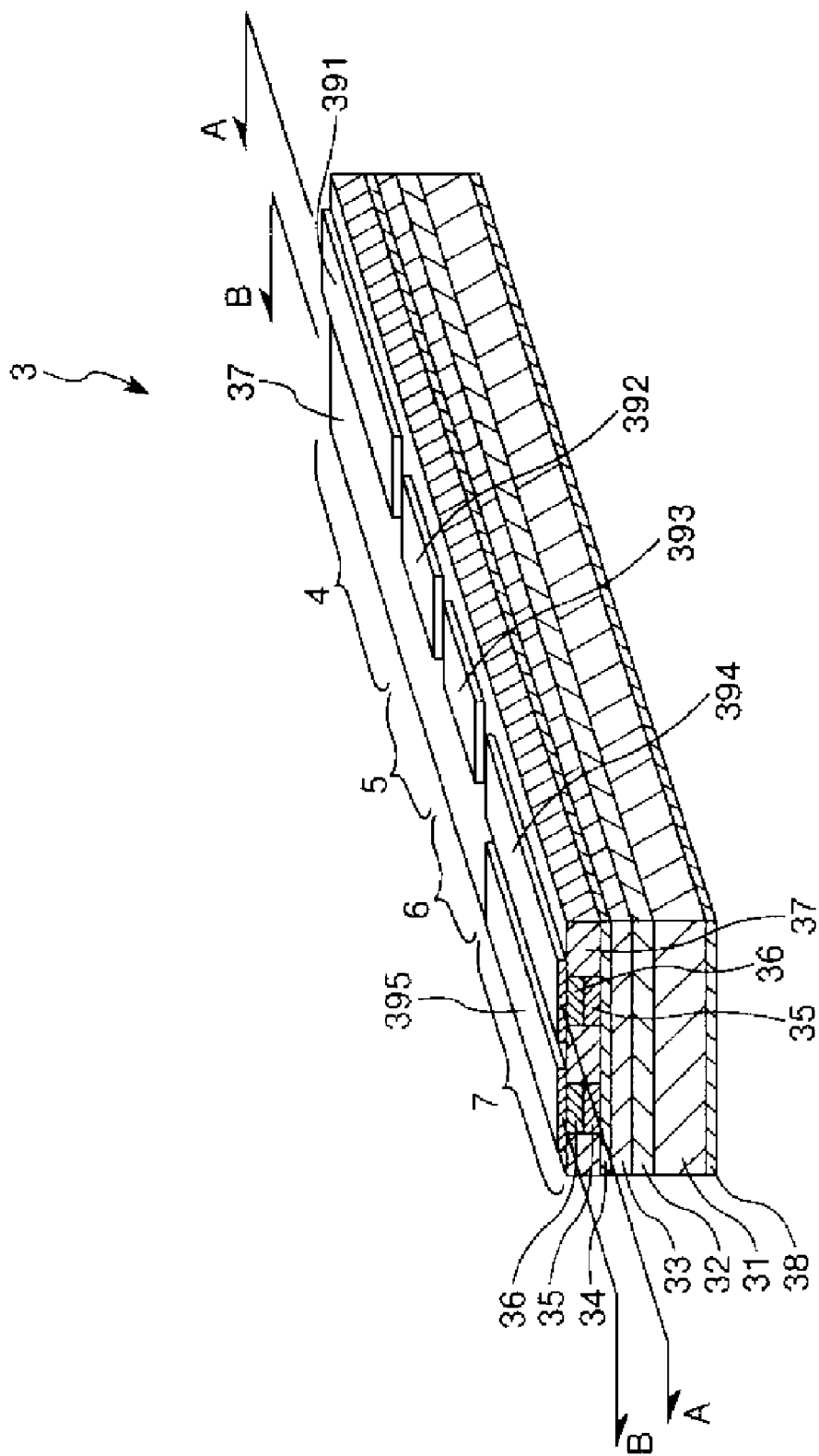
FIG. 2 is a cross-sectional perspective view of a light source device of a terahertz wave generation device illustrated in FIG. 1.
Figure 3:
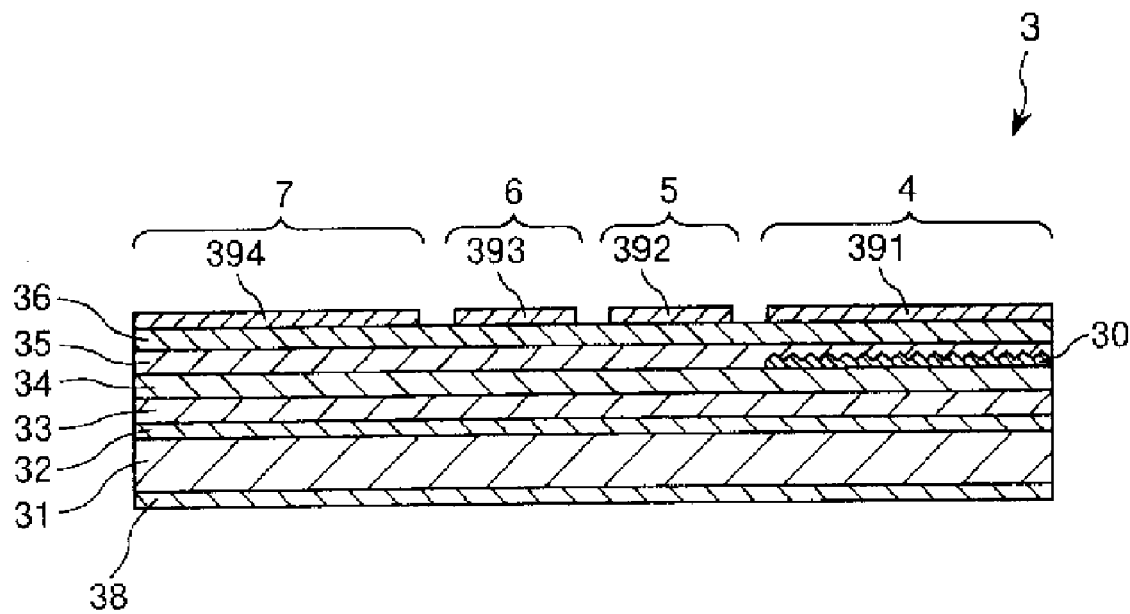
FIG. 3 is a cross-sectional view taken along line A-A of FIG. 2.
Figure 4:
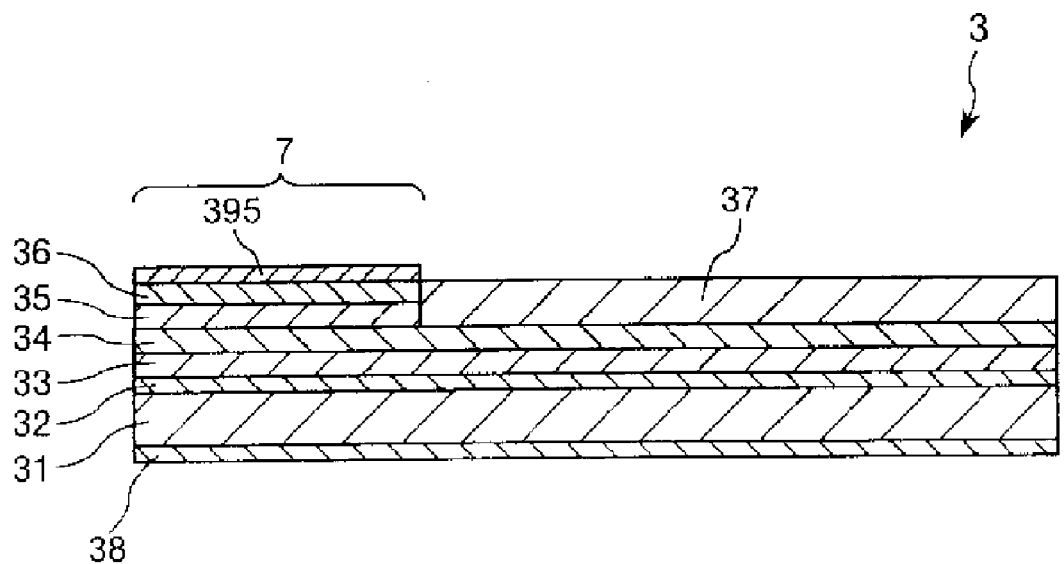
FIG. 4 is a cross-sectional view taken along line B-B of FIG. 2.

FIG. 1 is a diagram schematically illustrating a terahertz wave generation device according to a first embodiment of the invention. FIG. 2 is a cross-sectional perspective view of a light source device of a terahertz wave generation device illustrated in FIG. 1. FIG. 3 is a cross-sectional view taken along line A-A of FIG. 2, and FIG. 4 is a cross-sectional view taken along line B-B of FIG. 2.

As illustrated in FIG. 1, the terahertz wave generation device 1 includes a light source device 3 emitting an optical pulse, and an antenna 2 generating a terahertz wave via irradiation of the optical pulse that is emitted from the light source device 3 onto the antenna 2.

In this embodiment, the antenna 2 is a dipole-shaped photoconductive antenna (PCA), and includes a substrate 21 that is a semiconductor substrate, and a pair of electrodes 22 that are provided on the semiconductor substrate 21 and are oppositely arranged through a gap 23. If an optical pulse is irradiated between the electrodes 22, the antenna 2 generates a terahertz wave. In this case, a terahertz wave is an electromagnetic wave having frequencies equal to or greater than 100 GHz and equal to or less than 30 THz, and particularly, an electromagnetic wave having frequencies equal to or greater than 300 GHz and equal to or less than 3 THz.

Further, the distance between the pair of electrodes is not particularly limited, but is appropriately set depending on the terms and conditions. However, it is preferable that the distance between the electrodes 22 is equal to or greater than 1 μm and equal to or shorter than 10 μm.

As illustrated in FIGS. 2 to 4, the light source device 3 includes an optical pulse generation unit 4 generating the optical pulse, a first pulse compression unit 5 performing pulse compression with respect to the optical pulse generated by the optical pulse generation unit 4, a second pulse compression unit 7 performing pulse compression with respect to the optical pulse already compressed by the first pulse compression unit 5, and an amplifying unit 6 amplifying the optical pulse.

The amplifying unit 6 is installed at a front end of the first pulse compression unit 5 or between the first pulse compression unit 5 and the second pulse compression unit 7, and in the illustrated configuration, the amplifying unit 6 is installed between the first pulse compression unit 5 and the second pulse compression unit 7. Accordingly, the optical pulse already compressed by the first pulse compression unit 5 is amplified by the amplifying unit 6, and the optical pulse amplified by the amplifying unit 6 is pulse-compressed by the second pulse compression unit 7.

Further, the pulse width (half-value width) of the optical pulse that is emitted from the light source device 3 is not particularly limited, but it is preferable that the pulse width is equal to or greater than 10 femtoseconds and equal to or less than 800 femtoseconds.

Further, the optical pulse generation unit 4, for example, may use a DBR laser, a DFB laser, a mode-locked laser, and the like. The pulse width of the optical pulse that is generated by the optical pulse generation unit 4 is not particularly limited, but it is preferable that the pulse width is equal to or greater than 1 psec. and equal to or less than 100 psec.

Further, the first pulse compression unit 5 performs pulse compression based on the saturable absorber. That is, the first pulse compression unit 5 has saturable absorbers, and reduces the pulse width of the optical pulse by compressing the optical pulse through the saturable absorbers.

Further, the second pulse compression unit 7 performs pulse compression based on the group velocity dispersion compensation. That is, the first pulse compression unit 5 has a group velocity dispersion compensation medium, in this embodiment, a coupled waveguide structure, and reduces the pulse width of the optical pulse by compressing the optical pulse through the coupled waveguide structure.

Further, the optical pulse generation unit 4, the first pulse compression unit 5, the amplifying unit 6, and the second pulse compression unit 7 of the light source device 3 are integrally formed, that is, are integrated on the same substrate.

Specifically, the light source device 3 includes a substrate 31 that is a semiconductor substrate, a clad layer 32 installed on the substrate 31, an active layer 33 installed on the clad layer 32, an etching stop layer 34 for a waveguide configuration process installed on the active layer 33, a clad layer 35 installed on the etching stop layer 34 for the waveguide configuration process, a contact layer 36 installed on the clad layer 35, an insulating layer 37 installed on the etching stop layer 36 for the waveguide configuration process, an electrode 38 on the side of the clad layer 32 installed on the surface of the substrate 31, and electrodes 391, 392, 393, 394, and 395 on the side of the clad layer 35 installed on the surfaces of the contact layer 36 and the insulating layer 37. Further, a diffraction grating 30 is installed between the etching stop layer 34 for the waveguide configuration process of the second pulse compression unit 7 and the clad layer 35. In this case, the etching stop layer for the waveguide configuration process is not limited to be installed just on the active layer, but, for example, may be installed inside the clad layer.

In this case, the constituent materials of the respective units are not particularly limited, but, as an example, the substrate 31 and the contact layer 36 may be made of GaAs and the like. Further, the clad layers 32 and 35, the etching stop layer 36 for the waveguide configuration process, and the diffraction grating 30 may be made of, for example, AlGaAs and the like. Further, the active layer 33, for example, may be a configuration using a quantum effect that is called a multiple quantum well. Specifically, the active layer 33, for example, may be a structure that is called a distribution refractive index type multiple quantum well including multiple quantum wells and the like which are provided in a plurality by alternately installing well layers (GaAs well layers) and barrier layers (AlGaAs barrier layers).

Further, in the illustrated configuration, the waveguide of the light source device 3 includes the clad layer 32, the active layer 33, the etching stop layer 34 for the waveguide configuration process, and the clad layer 35. Further, the clad layer 35 is installed only on the upper portion of the waveguide in a shape corresponding to the waveguide. Further, the clad layer 35 is formed by removing an unnecessary portion by etching. In this case, depending on the manufacturing method, the etching stop layer 34 for the waveguide configuration process may be omitted.

Further, the clad layers 35 and the contact layers 36 are installed by twos. One clad layer 35 and the contact layer 36 form the optical pulse generation unit 4, the first pulse compression unit 5, the amplifying unit 6, and a part of the second pulse compression unit 7, and are continuously installed. The other clad layer 35 and the contact layer 36 form a part of the second pulse compression unit 7. That is, in the second pulse compression unit 7, a pair of clad layers 35 and a pair of contact layers 36 are installed.

Further, the electrode 391 is installed to correspond to the clad layer 35 of the optical pulse generation unit 4, and the electrode 392 is installed to correspond to the clad layer 35 of the first pulse compression unit 5. Further, the electrode 393 is installed to correspond to the clad layer 35 of the amplifying unit 6, and the electrodes 394 and 395 are installed to correspond to two clad layers 35 of the second pulse compression unit 7. In this case, the electrode 38 is a common electrode of the optical pulse generation unit 4, the first pulse compression unit 5, the amplifying unit 6, and the second pulse compression unit 7. Further, the electrode 38 and the electrode 391 form a pair of electrodes of the optical pulse generation unit 4, and the electrode 38 and the electrode 392 form a pair of electrodes of the first pulse compression unit 5. Further, the electrode 38 and the electrode 393 form a pair of electrodes of the amplifying unit 6, and the electrode 38 and the electrode 394, and the electrode 38 and the electrode 395 form two pairs of electrodes of the second pulse compression unit 7.

In this case, the entire shape of the light source device 3, in the illustrated configuration, forms a rectangular parallelepiped, but, needless to say, is not limited thereto.

Further, the dimensions of the light source device 3, being not particularly limited thereto, for example, may be equal to or greater than 1 mm and equal to or less than 10 mm×equal to or greater than 0.5 mm and equal to or less than 5 mm×equal to or greater than 0.1 mm and equal to or less than 1 mm.

Next, the operation of the terahertz wave generation device 1 will be described.

In the terahertz wave generation device 1, first, the optical pulse generation unit 4 of the light source device 3 generates the optical pulse. The pulse width of this optical pulse is larger than the target pulse width. The optical pulse that is generated by the optical pulse generation unit 4 sequentially penetrates the first pulse compression unit 5, the amplifying unit 6, and the second pulse compression unit 7 in that order through the waveguide.

First, the first pulse compression unit 5 performs the pulse compression based on saturable absorbers with respect to the optical pulse, and thus the pulse width of the optical pulse is reduced. Next, the amplifying unit 6 amplifies the optical pulse. Last, the second pulse compression unit 7 performs the pulse compression based on the group velocity distribution compensation with respect to the optical pulse, and thus the pulse width of the optical pulse is further reduced. In this way, the optical pulse having the target pulse width is generated to be emitted from the second pulse compression unit 7.

The optical pulse emitted from the light source device 3 is irradiated between the electrodes 22 of the antenna 2, and the terahertz wave is generated from the antenna 2.

As described above, according to the terahertz wave generation device 1, since the light source device 3 includes the first pulse compression unit 5, the amplifying unit 6, and the second pulse compression unit 7, miniaturization of the light source device 3, and further, miniaturization of the terahertz wave generation device 1, can be realized. Accordingly, the optical pulse having a desired pulse width at a desired height can be generated, and thus a desired terahertz wave can be certainly generated.

Second Embodiment

Figure 5:
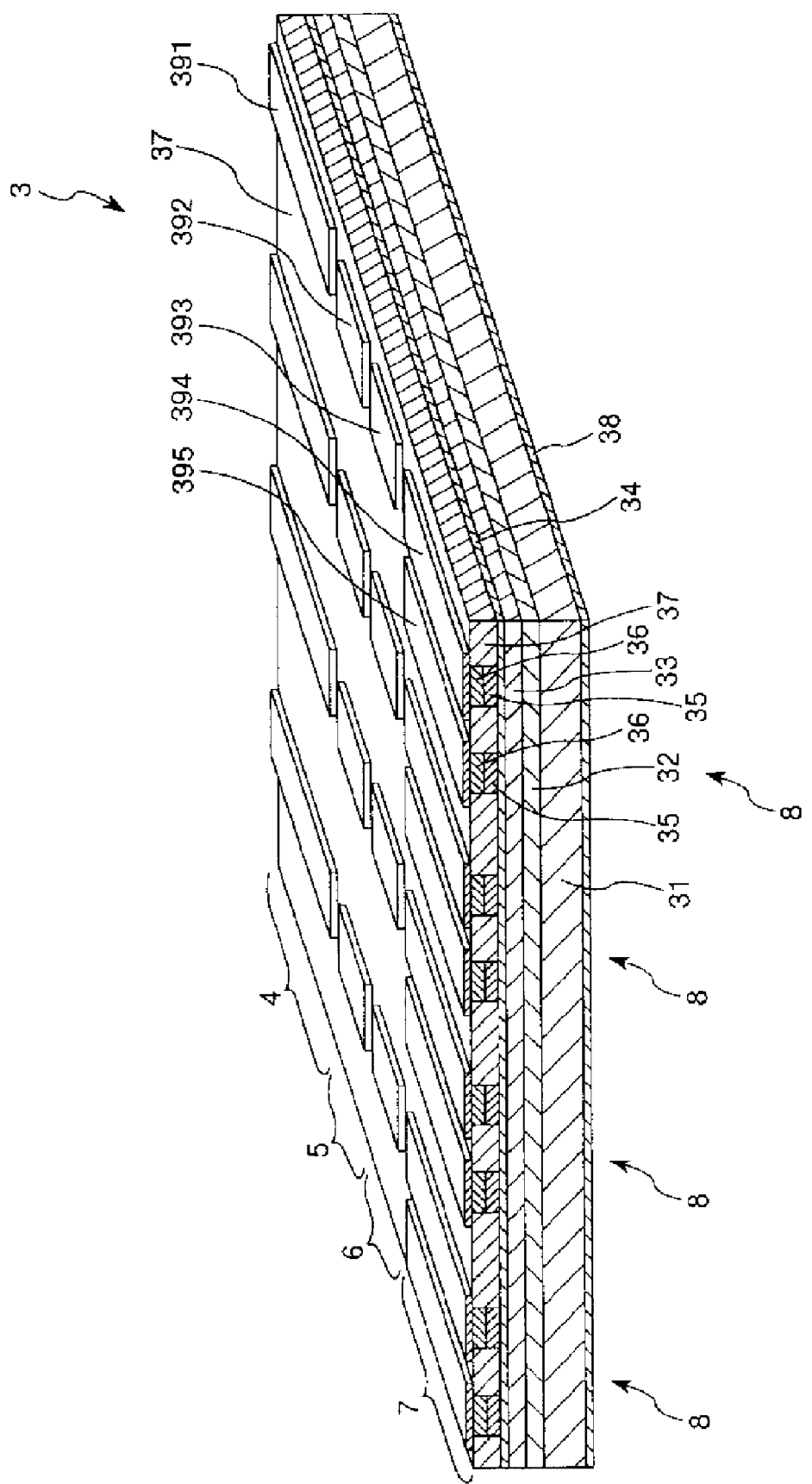
FIG. 5 is a cross-sectional perspective view of a light source device of a terahertz wave generation device according to a second embodiment of the invention.

FIG. 5 is a cross-sectional perspective view of a light source device of a terahertz wave generation device according to a second embodiment of the invention.

Hereinafter, the second embodiment will be described focusing mainly on the difference from the first embodiment as described above, and an explanation of common features will be omitted.

As illustrated in FIG. 5, in the terahertz wave generation device 1 according to the second embodiment, the light source device 3 includes plural units 8 each including the optical pulse generation unit 4, the first pulse compression unit 5, the amplifying unit 6, and the second pulse compression unit 7, and these units 8 are installed in parallel, that is, are arrayed. The respective units 8 correspond to the light source device 3 according to the first embodiment as described above.

Although four units 8 are used in the illustrated configuration, the embodiment is not limited thereto. The number of units 8 may be 2, 3, 5 or more.

Further, the optical pulses emitted from the respective units 8 are configured to be irradiated between the pair of electrodes that correspond to a common pair of electrodes 22 of the antenna 2. Accordingly, a high-output terahertz wave can be obtained.

Further, a higher-output terahertz wave can be obtained by preparing plural terahertz wave generation devices and synthesizing the terahertz waves generated by the respective terahertz wave generation devices 1.

In this case, to obtain the high-output terahertz wave by preparing plural terahertz wave generation devices 1 in which the antenna and the light source correspond to each other in a one-to-one manner and synthesizing the terahertz waves generated by the respective terahertz wave generation devices 1, it is necessary to prepare plural terahertz wave generation devices and to synthesize the terahertz waves generated by the plural terahertz wave generation devices 1, but it is very difficult to synthesize the terahertz waves. On the other hand, in the terahertz wave generation device 1 according to this embodiment, since the light source device 3 is arrayed and the output of the terahertz wave that is generated from one terahertz wave generation device 1 is high, the number of terahertz wave generation devices 1 that are used to obtain the high-output terahertz wave can be relatively small, and thus the synthesis of the terahertz waves can be easily and surely performed.

The second embodiment can be applied to a third embodiment, a fourth embodiment, and a fifth embodiment to be described later.

Third Embodiment

Figure 6:
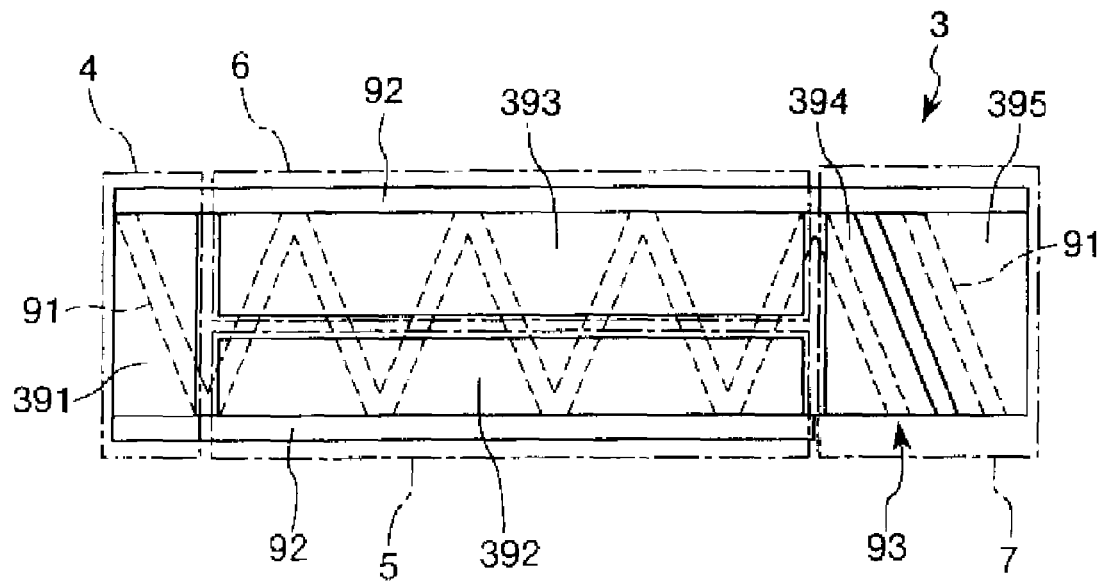
FIG. 6 is a plan view schematically showing a light source device of a terahertz wave generation device according to a third embodiment of the invention.

FIG. 6 is a plan view schematically illustrating a light source device of a terahertz wave generation device according to a third embodiment of the invention. In FIG. 6, the waveguide 91 is indicated by dashed lines, and the first pulse compression unit 5, the amplifying unit 6, and the second pulse compression unit 7 are surrounded by dashed lines, respectively.

Hereinafter, the third embodiment will be described focusing mainly on the difference from the first embodiment as described above, and an explanation of common features will be omitted.

As illustrated in FIG. 6, in the light source device 3 of the terahertz wave generation device 1 according to the third embodiment, the waveguides 91 are alternately bent several times. That is, the waveguide 91 is formed in a zigzag manner.

Further, the first pulse compression unit 5 is positioned on the lower side in FIG. 6, and the amplifying unit 6 is positioned on the upper side in FIG. 6. In the first pulse compression unit 5 and the amplifying unit 6, the respective waveguides 91 are bent several times. Further, on the boundary portion of the optical pulse generation unit 4 and the first pulse compression unit 5 and on the boundary portion of the amplifying unit 6 and the second pulse compression unit 7, the respective waveguides 91 are bent once.

Further, the light source device 3 has reflection films 92 formed on the bent portions of the waveguides 91 to reflect the optical pulses. The reflection films 92 are installed on the pair of side surfaces of the light source devices, respectively. The reflection films 92 can reflect the optical pulses so that the optical pulses travel along the waveguide 91.

In this case, the reflection film 92 is not installed in the optical pulse emission portion 93 of the light source device 3. Further, a reflection prevention film (not illustrated) may be installed in the emission portion 93.

According to the terahertz wave generation device 1, since the waveguides 91 of the light source device 3 are bent plural times, the length of the optical path, that is, the direct distance of the waveguide 91 can be lengthened, and thus the length of the light source device 3 can be shortened to seek further miniaturization of the device.

Fourth Embodiment

Figure 7:
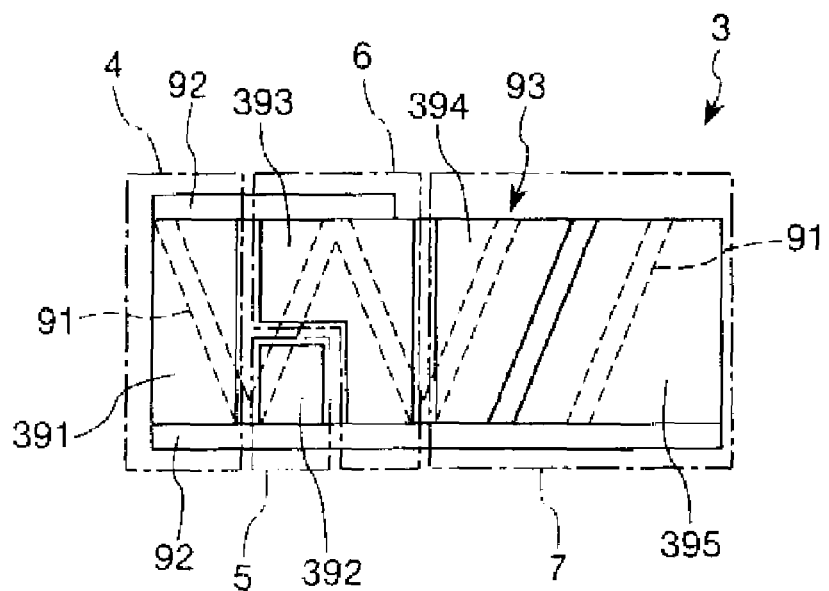
FIG. 7 is a plan view schematically showing a light source device of a terahertz wave generation device according to a fourth embodiment of the invention.

FIG. 7 is a plan view of a light source device of a terahertz wave generation device according to a fourth embodiment of the invention. In FIG. 7, the waveguide is indicated by dashed lines, and the first pulse compression unit 5, the amplifying unit 6, and the second pulse compression unit 7 are surrounded by dashed lines, respectively.

Hereinafter, the fourth embodiment will be described focusing mainly on the difference from the third embodiment as described above, and an explanation of common features will be omitted.

As illustrated in FIG. 7, in the light source device 3 of the terahertz wave generation device 1 according to the fourth embodiment, the waveguides 91 are alternately bent three times, and in the amplifying unit 6, the waveguide 91 is bent only once.

In the case where the amplifying unit 6 is installed at the front end of the first pulse compression unit 5, the waveguide 91 is bent only once in the first pulse compression unit 5.

Fifth Embodiment

Figure 8:
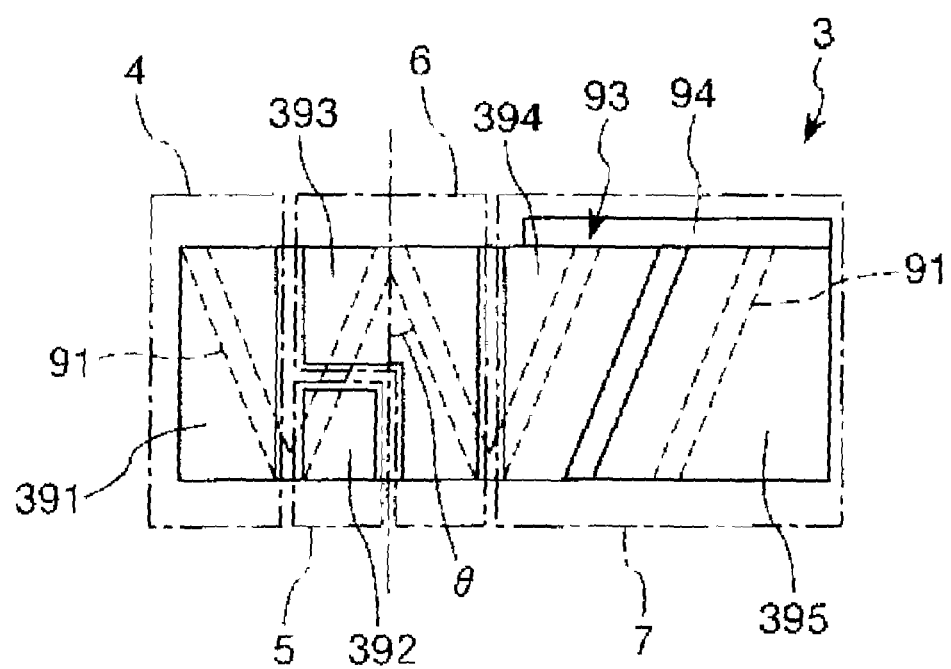
FIG. 8 is a plan view schematically showing a light source device of a terahertz wave generation device according to a fifth embodiment of the invention.

FIG. 8 is a plan view schematically illustrating a light source device of a terahertz wave generation device according to a fifth embodiment of the invention. In FIG. 8, the waveguide is indicated by dashed lines, and the first pulse compression unit 5, the amplifying unit 6, and the second pulse compression unit 7 are surrounded by dashed lines, respectively.

Hereinafter, the fifth embodiment will be described focusing mainly on the difference from the fourth embodiment as described above, and an explanation of common features will be omitted.

As illustrated in FIG. 8, in the light source device of the terahertz wave generation device 1 according to the fifth embodiment, the reflection film 92 is omitted.

Further, an angle θ shown in FIG. 8 in the bent portion of the waveguide 91 is set to be equal to or greater than a critical angle. Accordingly, the optical pulse can be reflected in a state where the reflection film 92 is not formed in the bent portion of the waveguide 91, and thus the structure can be simplified.

Further, the reflection prevention film 94 is installed in the optical pulse emission portion 93 of the light source device 3. Accordingly, the optical pulse can be emitted from the emission portion 93.

The fifth embodiment can also be applied to the third embodiment.

Embodiment of an Image Device

Figure 9:
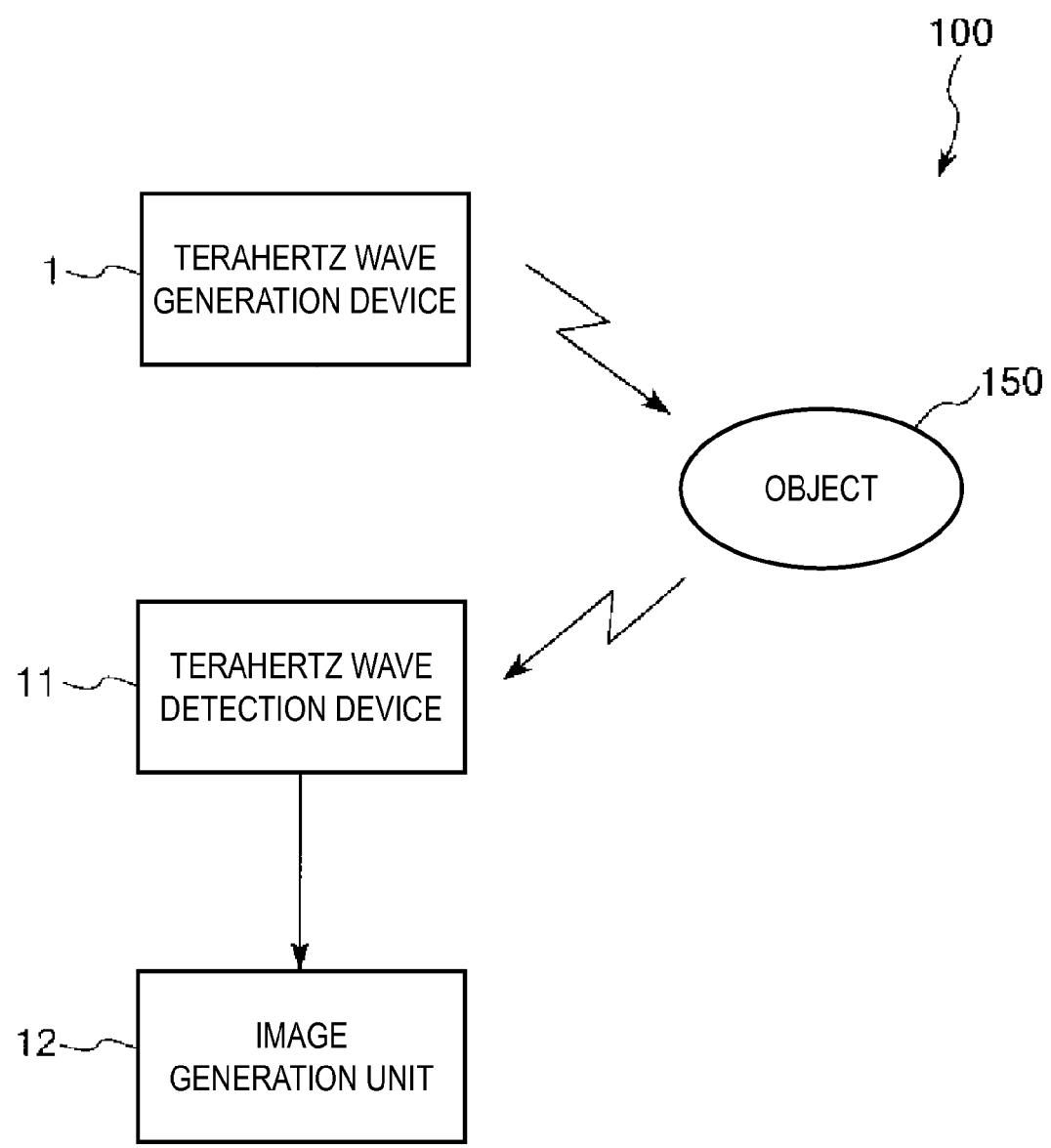
FIG. 9 is a block diagram illustrating an imaging device according to an embodiment of the invention.
Figure 10:
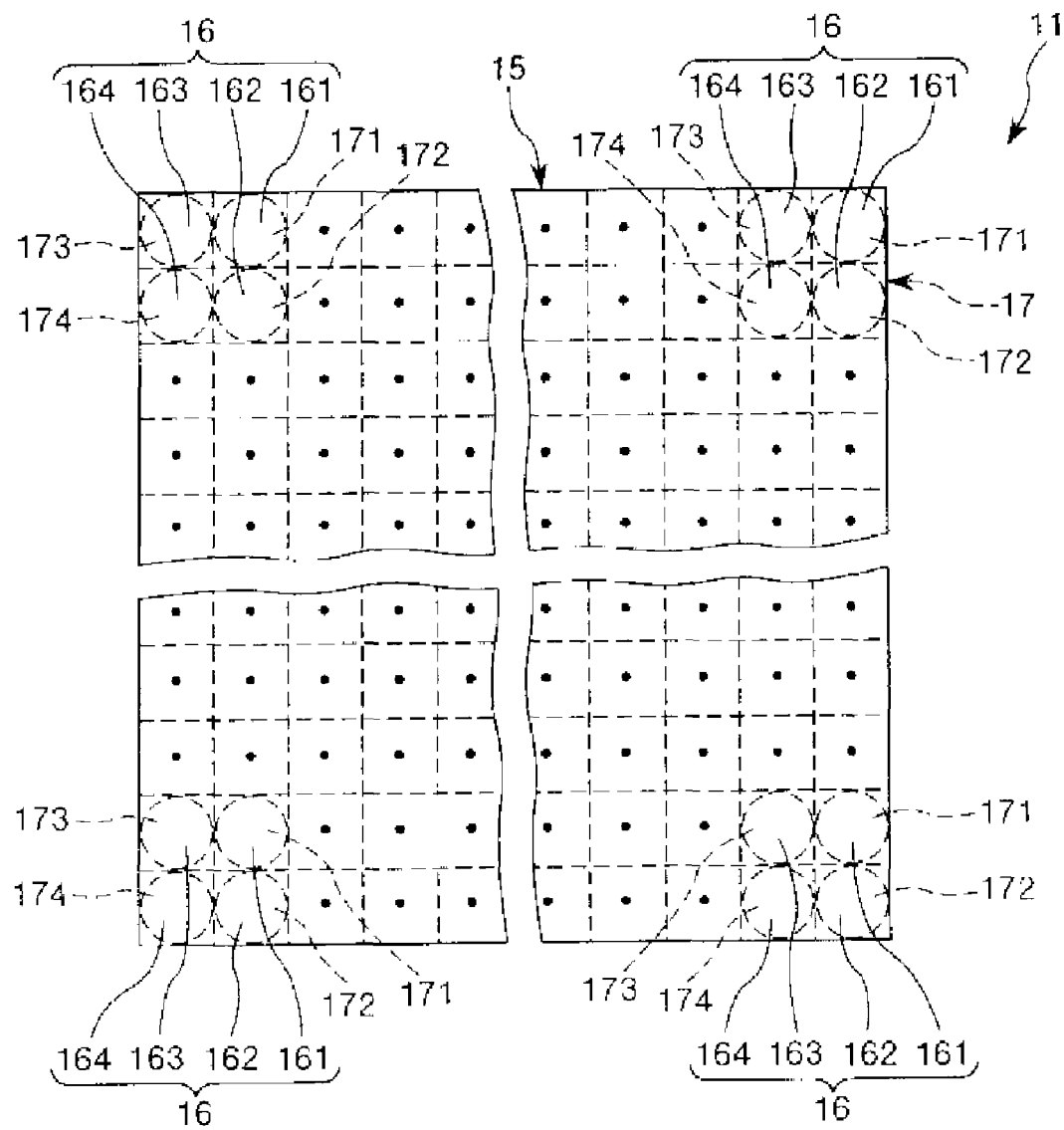
FIG. 10 is a plan view illustrating a terahertz detection device of an image device illustrated in FIG. 9.

FIG. 9 is a block diagram illustrating an imaging device according to an embodiment of the invention. FIG. 10 is a plan view illustrating a terahertz wave detection device of an image device illustrated in FIG. 9.

As illustrated in FIG. 9, the imaging device 100 includes a terahertz wave generation device 1 generating a terahertz wave, a terahertz wave detection device 11 detecting the terahertz wave that is emitted from the terahertz wave generation device 1 and penetrates or is reflected from an object 150, and an image generation unit 12 generating an image of the object 150, that is, image data, based on the result of the detection performed by the terahertz wave detection device 11.

As the terahertz wave generation device 1, in this embodiment, any one of the first to fifth embodiments may be used.

Further, the terahertz wave detection device 11, for example, includes a filter 15 through which the terahertz wave having a target wavelength passes, and a detection unit 17 detecting the terahertz wave having the target wavelength that has passed through the filter 15 by converting the terahertz wave into heat. Further, the detection unit 17, for example, detects the terahertz wave by converting the terahertz wave into heat, that is, converts the terahertz wave into heat and detects energy (intensity) of the terahertz wave. The detection unit, for example, may be a pyroelectric sensor or a bolometer. Of course, the terahertz wave detection device 11 is not limited to the above-described configuration.

Further, the filter 15 includes plural pixels (unit filter portions) 16 which are two-dimensionally arranged. That is, the respective pixels 16 are arranged in the form of a matrix.

Further, each pixel 16 has plural areas through which terahertz waves having different wavelengths pass, that is, each pixel has plural areas having different wavelengths (hereinafter also referred to as a "pass wavelength") of the terahertz waves that pass through the areas. In the illustrated configuration, each pixel 16 includes a first area 161, a second area 162, a third area 163, and a fourth area 164.

Further, the detection unit 17 includes a first unit detection portion 171, a second unit detection portion 172, a third unit detection unit 173, and a fourth unit detection 174, which are installed to correspond respectively to the first area 161, the second area 162, the third area 163, and the fourth area 164 of each pixel 16 of the filter 15. The first unit detection portion 171, the second unit detection portion 172, the third unit detection portion 173, and the fourth unit detection portion 174 detect the terahertz waves that have passed respectively through the first area 161, the second area 162, the third area 163, and the fourth area 164 of each pixel 16 through conversion of the terahertz waves into heat. Accordingly, each pixel 16 can surely detect the terahertz waves having four desired wavelengths.

Next, an exemplary use of the imaging device 100 will be described.

First, an object 150 that is the subject of spectral imaging is composed of three materials A, B, and C. The imaging device 100 performs spectral imaging of the object 150. Here, as an example, the terahertz wave detection device 1 detects the terahertz waves that are reflected from the object 150.

Figure 11:
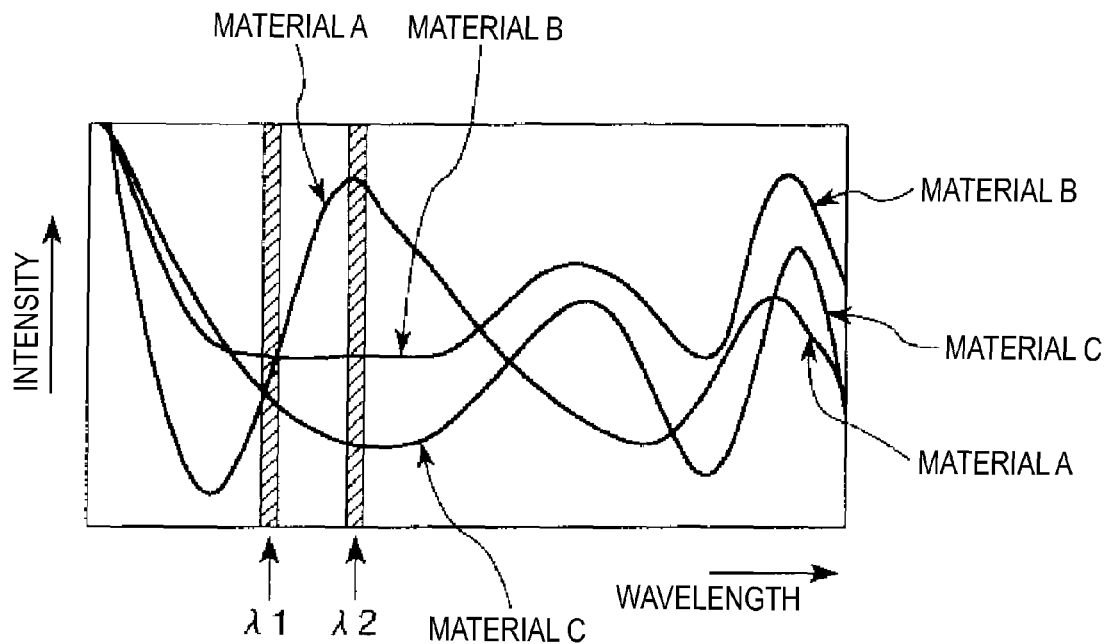
FIG. 11 is a graph illustrating spectrums in a terahertz band of an object.

FIG. 11 is a graph illustrating spectrums in the terahertz band of the object 150.

In each pixel 16 of the filter 15 of the terahertz wave detection device 1, the first area 161 and the second area 162 are used.

Further, if it is assumed that the pass wavelength of the first area 161 is $\lambda 1$, the pass wavelength of the second area 162 is $\lambda 2$, the intensity of a component of the wavelength $\lambda 1$ of the terahertz wave that is reflected from the object 150 is $\alpha 1$, and the intensity of a component of the wavelength $\lambda 2$ is $\alpha 2$, the path wavelength $\lambda 1$ of the first area 161 and the pass wavelength $\lambda 2$ of the second area 162 are set so that the difference ($\alpha 2 - \alpha 1$) between the intensity $\alpha 2$ and the intensity a1 can be remarkably distinct in the materials A, B, and C.

As illustrated in FIG. 11, the difference ($\alpha 2 - \alpha 1$) between the intensity $\alpha 2$ of the component of the wavelength $\lambda 2$ of the terahertz wave that is reflected from the object 150 and the intensity $\alpha 1$ of the component of the wavelength $\lambda 1$ becomes a positive value in the material A.

Further, the difference ($\alpha 2 - \alpha 1$) between the intensity $\alpha 2$ and the intensity $\alpha 1$ becomes 0 in the material B.

Further, the difference ($\alpha 2 - \alpha 1$) between the intensity $\alpha 2$ and the intensity $\alpha 1$ becomes a negative value in the material C.

When the spectral imaging of the object 150 is performed by the imaging device 100, first, the terahertz wave is generated by the terahertz wave generation device 1, and the generated terahertz wave is irradiated onto the object 150. Further, the terahertz wave reflected from the object 150 is detected by the terahertz wave detection device 11. The result of this detection is sent to the image generation unit 12. In this case, the irradiation of the terahertz wave onto the object 150 and the detection of the terahertz wave that is reflected from the object 150 are performed with respect to the entire object 150.

Based on the result of the detection, the image generation unit 12 obtains the difference ($\alpha 2 - \alpha 1$) between the intensity $\alpha 2$ of the component of the wavelength $\lambda 2$ of the terahertz wave that has passed through the second area 162 of the filter 15 and the intensity $\alpha 1$ of the component of the wavelength $\lambda 1$ of the terahertz wave that has passed through the first area 161. Thereafter, the image generation unit 12 determines and identifies that a region in which the difference becomes a positive value is material A, a region in which the difference becomes 0 is material B, and a region in which the difference becomes a negative value is material C in the object 150.

Figure 12:
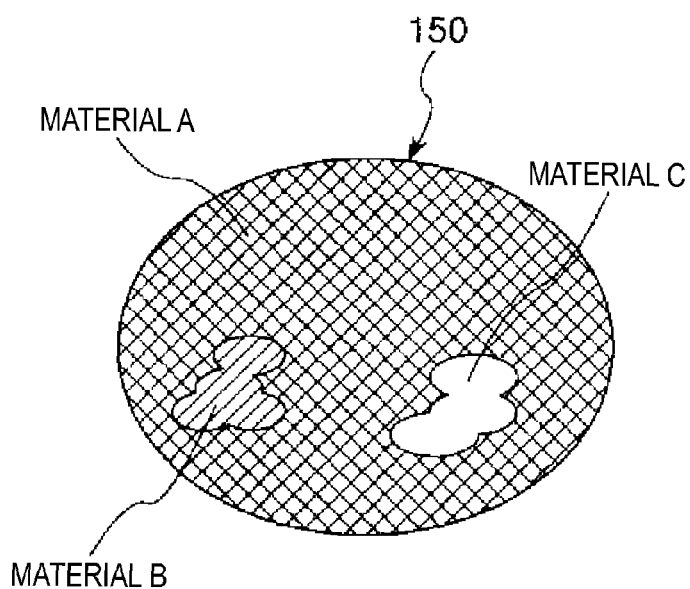
FIG. 12 is a diagram illustrating an image that indicates distribution of materials A, B, and C of an object.

Further, as illustrated in FIG. 12, the image generation unit 12 prepares image data of an image that indicates distribution of the materials A, B, and C of the object 150. This image data is sent from the image generation unit 12 to a monitor (not illustrated), and the image that indicates the distribution of the materials A, B, and C of the object 150 is displayed on the monitor. In this case, for example, the area in which the material A of the object 150 is distributed appears black, the area in which the material B is distributed appears gray, and the area in which the material C is distributed appears white, respectively. As described above, the imaging device 100 can simultaneously perform the identification of the respective materials that constitute the object 150 and the distribution measurement of the respective materials.

The use of the imaging device 100 is not limited to those described above. For example, by irradiating a person with the terahertz wave, detecting the terahertz wave that penetrates or is reflected from the person, and performing the process through the image generation unit 12, it may be determined whether or not the person possesses a pistol, a knife, or illicit drugs.

Embodiment of a Measurement Device

Figure 13:
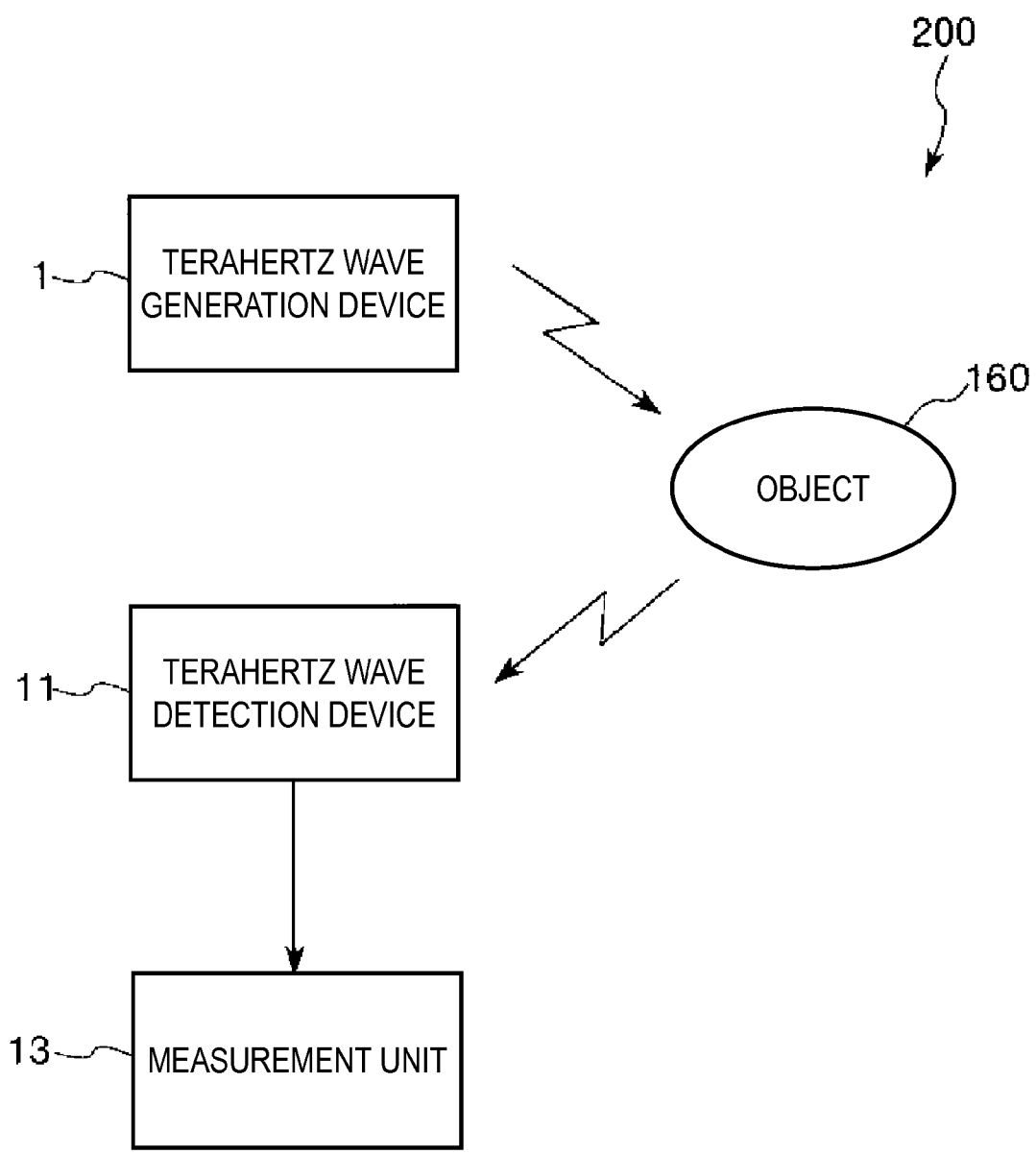
FIG. 13 is a block diagram illustrating a measurement device according to an embodiment of the invention.

FIG. 13 is a block diagram illustrating a measurement device according to an embodiment of the invention.

Hereinafter, the measurement device according to an embodiment will be described focusing mainly on the difference from the imaging device according to an embodiment as described above, and an explanation of common features will be omitted.

As illustrated in FIG. 13, the measurement device 200 includes the terahertz wave generation device 1 generating the terahertz wave, the terahertz wave detection device 11 detecting the terahertz wave that is emitted from the terahertz wave generation device 1 and penetrates or is reflected from the object 160, and the measurement unit 13 measuring the object 160 based on the result of the detection performed by the terahertz wave detection device 11.

Next, an exemplary use of the measurement device 200 will be described.

When the spectral measurement of the object 160 is performed by the measurement device 200, first, the terahertz wave is generated by the terahertz wave generation device 1, and the generated terahertz wave is irradiated onto the object 160. Further, the terahertz wave that penetrates or is reflected from the object 160 is detected by the terahertz wave detection device 11. The result of this detection is sent to the measurement unit 13. In this case, the irradiation of the terahertz wave onto the object 160 and the detection of the terahertz wave that penetrates or is reflected from the object 160 are performed with respect to the entire object 160.

The measurement unit 13 determines the respective intensities of the terahertz waves which have passed through the first area 161, the second area 162, the third area 163, and the fourth area 164 of the filter 15 from the result of the detection, and performs analysis of the components and the component distribution of the object 160.

Embodiment of a Camera

Figure 14:
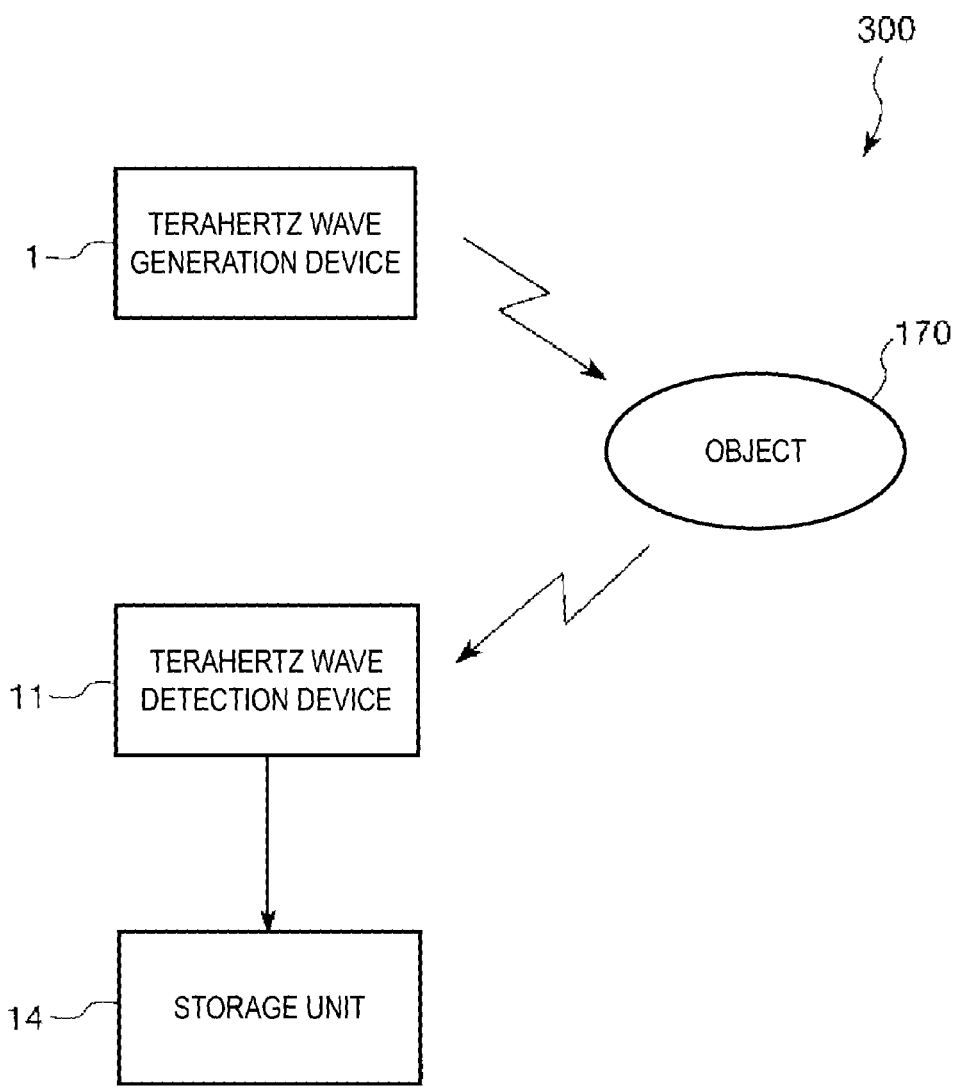
FIG. 14 is a block diagram illustrating a camera according to an embodiment of the invention.

FIG. 14 is a block diagram illustrating a camera according to an embodiment of the invention.

Hereinafter, the camera according to an embodiment will be described focusing mainly on the difference from the imaging device according to an embodiment as described above, and an explanation of common features will be omitted.

As illustrated in FIG. 14, the camera 300 includes the terahertz wave generation device 1 generating the terahertz wave, and the terahertz wave detection device 11 detecting the terahertz wave that is emitted from the terahertz wave generation device 1 and penetrates or is reflected from the object 170.

Next, an exemplary use of the camera 300 will be described.

When the object 170 is captured by the camera 300, first, the terahertz wave is generated by the terahertz wave generation device 1, and the generated terahertz wave is irradiated onto the object 170. Further, the terahertz wave that penetrates or is reflected from the object 170 is detected by the terahertz wave detection device 11. The result of this detection is sent to the storage unit 14 to be stored. In this case, the irradiation of the terahertz wave onto the object 170 and the detection of the terahertz wave that penetrates or is reflected from the object 170 are performed with respect to the entire object 170. Further, the result of the detection, for example, may be transmitted to an external device such as a personal computer. The personal computer may perform respective processes on the basis of the result of the detection.

Although the terahertz wave generation device, the camera, the imaging device, and the measurement device according to the embodiments of the invention have been described, the invention is not limited thereto. The configurations of the respective units may be replaced by configurations having the same functions. Further, other configurations may be added to the invention.

Further, the invention may be a combination of any two or more of configurations (features) of the above-described embodiments.

In this case, in the light source device 3, the optical pulse generation unit may be separately provided.

What is claimed is:

1. A terahertz wave generation device comprising:
   a light source device emitting an optical pulse; and
   an antenna irradiated with the optical pulse emitted from the light source and responsively generating a terahertz wave,
   wherein the light source device includes:
     an optical pulse generation unit generating the optical pulse;
     a first pulse compression unit performing pulse compression with saturable absorbers on the optical pulse generated by the optical pulse generation unit;
     a second pulse compression unit performing pulse compression with group velocity dispersion compensation on the optical pulse already compressed by the first pulse compression unit; and
     an amplifying unit installed between the first pulse compression unit and the second pulse compression unit to amplify the optical pulse emitted from the first pulse compression unit.

2. The terahertz wave generation device according to claim 1, wherein the first pulse compression unit has a waveguide with at least one bend.

3. The terahertz wave generation device according to claim 2, wherein the first pulse compression unit has a reflection film formed on the bend of the waveguide to reflect the optical pulse.

4. The terahertz wave generation device according to claim 1, wherein the amplifying unit has a waveguide with at least one bend.

5. The terahertz wave generation device according to claim 4, wherein the amplifying unit has a reflection film formed on the bend of the waveguide to reflect the optical pulse.

6. The terahertz wave generation device according to claim 1, wherein the light source device is provided with plural units each including the optical pulse generation unit, the first pulse compression unit, the second pulse generation unit, and the amplifying unit.

7. A terahertz wave generation device comprising:
a light source device emitting an optical pulse; and
an antenna irradiated with the optical pulse emitted from the light source and responsively generating a terahertz wave,
wherein the light source device includes:
an optical pulse generation unit generating the optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the optical pulse generation unit and the first pulse compression unit to amplify the optical pulse emitted from the optical pulse generation unit.

8. The terahertz wave generation device according to claim 7, wherein the first pulse compression unit has a waveguide with at least one bend.

9. The terahertz wave generation device according to claim 8, wherein the first pulse compression unit has a reflection film formed on the bend of the waveguide to reflect the optical pulse.

10. The terahertz wave generation device according to claim 7, wherein the amplifying unit has a waveguide with at least one bend.

11. The terahertz wave generation device according to claim 10, wherein the amplifying unit has a reflection film formed on the bend of the waveguide to reflect the optical pulse.

12. The terahertz wave generation device according to claim 7, wherein the light source device is provided with plural units each including the optical pulse generation unit, the first pulse compression unit, the second pulse generation unit, and the amplifying unit.

13. A light source device comprising:
an optical pulse generation unit generating an optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the first pulse compression unit and the second pulse compression unit to amplify the optical pulse emitted from the first pulse compression unit.

14. The light source device according to claim 13, wherein the first pulse compression unit has a waveguide with at least one bend.

15. The light source device according to claim 14, wherein the first pulse compression unit has a reflection film formed on the bend of the waveguide to reflect the optical pulse.

16. The light source device according to claim 13, wherein the amplifying unit has a waveguide with at least one bend.

17. The light source device according to claim 16, wherein the amplifying unit has a reflection film formed on the bend of the waveguide to reflect the optical pulse.

18. The light source device according to claim 13, wherein the light source device is provided with plural units each including the optical pulse generation unit, the first pulse compression unit, the second pulse generation unit, and the amplifying unit.

19. A light source device comprising:
an optical pulse generation unit generating an optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the optical pulse generation unit and the first pulse compression unit to amplify the optical pulse generated from the optical pulse generation unit.

20. The light source device according to claim 19, wherein the first pulse compression unit has a waveguide with at least one bend.

21. The light source device according to claim 20, wherein the first pulse compression unit has a reflection film formed on the bend of the waveguide to reflect the optical pulse.

22. The light source device according to claim 19, wherein the amplifying unit has a waveguide with at least one bend.

23. The light source device according to claim 22, wherein the amplifying unit has a reflection film formed on the bend of the waveguide to reflect the optical pulse.

24. The light source device according to claim 19, wherein the light source device is provided with plural units each including the optical pulse generation unit, the first pulse compression unit, the second pulse generation unit, and the amplifying unit.

25. A camera comprising:
a terahertz wave generation device emitting a terahertz wave; and
a terahertz wave detection device detecting the terahertz wave that is emitted from the terahertz wave generation device and penetrates or is reflected from an object,
wherein the terahertz wave generation device includes:
a light source device emitting an optical pulse; and
an antenna irradiated with the optical pulse emitted from the light source and responsively generating a terahertz wave,
wherein the light source device has:
an optical pulse generation unit generating the optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the first pulse compression unit and the second pulse compression unit to amplify the optical pulse emitted from the first pulse compression unit.

26. A camera comprising:
a terahertz wave generation device emitting a terahertz wave; and
a terahertz wave detection device detecting the terahertz wave that is emitted from the terahertz wave generation device and penetrates or is reflected from an object,
wherein the terahertz wave generation device includes:

a light source device emitting an optical pulse; and
an antenna irradiated with the optical pulse emitted from the light source and responsively generating a terahertz wave,
wherein the light source device has:
an optical pulse generation unit generating the optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the optical pulse generation unit and the first pulse compression unit to amplify the optical pulse generated from the optical pulse generation unit.

27. An imaging device comprising:
a terahertz wave generation device emitting a terahertz wave;
a terahertz wave detection device detecting the terahertz wave that is emitted from the terahertz wave generation device and penetrates or is reflected from an object; and
an image generation unit generating an image of the object based on the result of the detection performed by the terahertz wave detection device,
wherein the terahertz wave generation device includes:
a light source device emitting an optical pulse; and
an antenna irradiated with the optical pulse emitted from the light source and responsively generating a terahertz wave,
wherein the light source device has:
an optical pulse generation unit generating the optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the first pulse compression unit and the second pulse compression unit to amplify the optical pulse emitted from the first pulse compression unit.

28. An imaging device comprising:
a terahertz wave generation device emitting a terahertz wave;
a terahertz wave detection device detecting the terahertz wave that is emitted from the terahertz wave generation device and penetrates or is reflected from an object; and
an image generation unit generating an image of the object based on the result of the detection performed by the terahertz wave detection device,
wherein the terahertz wave generation device includes:
a light source device emitting an optical pulse; and
an antenna irradiated with the optical pulse emitted from the light source and responsively generating a terahertz wave,
wherein the light source device has:
an optical pulse generation unit generating the optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the optical pulse generation unit and the first pulse compression unit to amplify the optical pulse generated from the optical pulse generation unit.

29. A measurement device comprising:
a terahertz wave generation device emitting a terahertz wave;
a terahertz wave detection device detecting the terahertz wave that is emitted from the terahertz wave generation device and penetrates or is reflected from an object; and
a measurement unit measuring the object based on the result of the detection performed by the terahertz wave detection device,
wherein the terahertz wave generation device includes:
a light source device emitting an optical pulse; and
an antenna irradiated with the optical pulse emitted from the light source and responsively generating a terahertz wave,
wherein the light source device has:
an optical pulse generation unit generating the optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the first pulse compression unit and the second pulse compression unit to amplify the optical pulse emitted from the first pulse compression unit.

30. A measurement device comprising:
a terahertz wave generation device emitting a terahertz wave;
a terahertz wave detection device detecting the terahertz wave that is emitted from the terahertz wave generation device and penetrates or is reflected from an object; and
a measurement unit measuring the object based on the result of the detection performed by the terahertz wave detection device,
wherein the terahertz wave generation device includes:
a light source device emitting an optical pulse; and
an antenna irradiated with the optical pulse emitted from the light source and responsively generating a terahertz wave,
wherein the light source device has:
an optical pulse generation unit generating the optical pulse;
a first pulse compression unit performing pulse compression with saturable absorbers on the optical pulse generated by the optical pulse generation unit;
a second pulse compression unit performing pulse compression with group velocity dispersion compensation on the optical pulse already compressed by the first pulse compression unit; and
an amplifying unit installed between the optical pulse generation unit and the first pulse compression unit to amplify the optical pulse generated from the optical pulse generation unit.

* * * * *